(12) United States Patent
Wang

(10) Patent No.: US 7,993,893 B2
(45) Date of Patent: Aug. 9, 2011

(54) HAEMOCOAGULASE

(75) Inventor: Xijuan Wang, Beijing (CN)

(73) Assignee: Konruns Pharmaceutical Co., Ltd, Beijing (CN)

( * ) Notice: Subject to any disclaimer, the term of this patent is extended or adjusted under 35 U.S.C. 154(b) by 88 days.

(21) Appl. No.: 12/446,182

(22) PCT Filed: Dec. 8, 2006

(86) PCT No.: PCT/CN2006/003353
§ 371 (c)(1),
(2), (4) Date: Apr. 20, 2009

(87) PCT Pub. No.: WO2008/046256
PCT Pub. Date: Apr. 24, 2008

(65) Prior Publication Data
US 2010/0120120 A1  May 13, 2010

(30) Foreign Application Priority Data
Oct. 19, 2006  (CN) .......................... 2006 1 0150566

(51) Int. Cl.
*C12N 9/00* (2006.01)
(52) U.S. Cl. ...................................................... 435/183
(58) Field of Classification Search .................. None
See application file for complete search history.

(56) References Cited

FOREIGN PATENT DOCUMENTS
| CN | 1534093 A | | 10/2004 |
|---|---|---|---|
| WO | WO 99/29838 | * | 6/1999 |
| WO | 2005017139 A1 | | 2/2005 |

OTHER PUBLICATIONS

Castro et al., "Snake venom thrombin-like enzymes: from reptilase to now", Cell. Mol. Life Sci., 2004, vol. 61, pp. 843-856.*
Nobuyuki Itoh et al "Molecular Cloning and Sequence Analysis of cDNA for Batroxobin, a Thrombin-like Snake Venom Enzyme" J. Biol. Chem. Mar. 5, 1987, vol. 262, No. 7, pp. 3132-3135.
Nobuyuki Itoh et al "Organization of the Gene for Batroxobin, a Thrombin-like Snake Venom Enzyme" J. Biol. Chem. Jun. 5, 1988, vol. 263, No. 16, pp. 7628-7631.
Nobuyuki Itoh et al "The complete nucleotide sequence of the gene for batroxobin, a thrombin-like snake venom enzyme" Nucleic Acids Res. Nov. 11, 1988, Vo. 16, No. 21, pp. 10377-10378.

* cited by examiner

*Primary Examiner* — Suzanne M. Naokes
(74) *Attorney, Agent, or Firm* — Workman Nydegger

(57) ABSTRACT

The present invention provides a venene haemocoagulase gene and its expression for the functional protein. The haemocoagulase gene of the present invention has a nucleotide sequence shown by the sequence list SEQ ID NO: 1 or the mutated nucleotide sequence formed by replacement, depletion, or addition of one or more nucleotide based on the said nucleotide sequence with an equivalent function. The said haemocoagulase has amino acid sequence shown by SEQ ID NO: 2. Haemocoagulase of the present invention has an obvious hemostatic effect, a broad effective dose range, safe and reliable application, which creates good conditions for the development of genetic engineering products of recombinant haemocoagulase in the future.

6 Claims, 1 Drawing Sheet

US 7,993,893 B2

HAEMOCOAGULASE

TECHNICAL FIELD

The invention belongs to the field of biotechnology, specifically relates to a venene protein, haemocoagulase and its encoding gene.

BACKGROUND ART

Reptilase, also called haemocoagulase, is a novel haemostat drug with clinical application in recent years. It is an enzymatic haemostat isolated from the venom of fer-de-lance (Bothrops Atrox) and contains two active ingredients, batroxobin and clauden (a phospholipid-depending Factor X Acitivator). Batroxobin in reptilase stimulates the degradation of fibrinogen into fibinopeptide A and increased number of defibrination monomers which could linked to form fibrin I multimers. Haemocoagulase has an effect on the process of the cross-linked fibrin formation by fibrin I multimers, which results in the function of hemostasis. The fibrin I multimer can also stimulate platelet aggregation around vascular lesions and accelerate the formation of platelet tampon, thereby accelerating the effect of hemostasis at the site of vascular lesions. Clauden in reptilase can activate the Blood coagulation factor X which were concentrating on the surface of phospholipid reaction and then convert it into blood coagulation factor Xa. Factor Xa could then form a complex prothrombin activator together with calcium ion, blood coagulation factor Va and platelet phospholipid (PF3). This complex prothrombin activator catalyzes conversion of prothrombin to thrombin at the vascular lesions, thereby promoting the formation of blood clotting and thrombus. Reptilase does not induce blood clotting of the blood vessels with a usual dose. It has the effect of hemostasis only under the condition of bleeding, and it shows good therapeutic effect during the clinical application.

There are abundant research resources on snake venom in China. It has been reported that a special haemocoagulase with hemostasis effect can be isolated and purified from the snake venom of Agkistrodon acutus in China. However, due to the complicated components in the snake venom, there are two disadvantages of the biochemical venom products obtained by biochemical process: a) the whole operation is costly and difficult, b) other residue components after the process of purification may lead to different therapeutic effects and toxic side effects.

Therefore, genetic engineering was introduced into the study of batroxobin. The first application was in 1991. cDNA of batroxobin was isolated from the cDNA library of B. atroxmoojeni by Maeda etc., and was cloned into the expression vector of E. coli by recombination. Fusion proteins were expressed in the form of inclusion, and part of natural activities was obtained by refolding. However, the expression of mature and functional protein of batroxobin was not detected. In terms of structure, most batroxobins are glycoproteins. The expressed product can not be glycosylated due to the limit of the E. coli expression system itself, that is, lacking the function of posttranslational processing of proteins which is very important to protein intrinsic property and its biological functions. In 1996, Ancrod, a batroxobin originating from agkistroclon rlzodoston, was successfully expressed in epidermal cells of mice by Geyei etc. It was the first time that batroxobin was expressed in mammalian cells. It also showed that the structure of glycosylation is closer to that of the natural enzyme. Subsequently, batroxobin genes were cloned into pichia yeast to obtain a secreted product, Gussurobin, which also showed a higher biological activity. Therefore, it is generally believed that the expression of batroxobin genes should be performed inside the eucaryotic expression system.

CONTENT OF THE INVENTION

The object of the present invention is to obtain and provide a valid haemocoagulase with good haemostatic effect from Agkistrodon acutus, as well as its encoding genes.

The nucleotide sequence of haemocoagulase gene of Agkistrodon acutus according to the present invention (which will now be referred to as SL32 gene) is shown by sequence list SEQ ID NO: 1. The amino acid sequence of protein encoded by above-mentioned gene is shown by sequence list SEQ ID NO: 2. The present invention further includes the amino acid sequences that are formed by replacing, depleting, or adding one or more amino acids according to the amino acid sequence shown by SEQ ID NO: 2 and possess an equivalent function and their encoding nucleotide sequences.

There is a high homology between the SL32 gene and mRNA of batroxobin (gi:211023. SL32 gene has 1326 base pairs, and the mRNA of batroxobin has 1504 base pairs. SL32 encodes the protein with 255 amino acids, batroxobin also has 255 amino acids. The difference between them is that the eleventh N-terminal amino acid is glutamine (Q) in SL32, while it is leucine (L) in the primary structure of batroxobin.

Although proteins encoded by the SL32 gene seems to be very similar to batroxobin, they have significantly different activity due to their different origins and definitely different nucleic acid sequence and primary structure of amino acids. The 30 amino acids at N-terminus of SL32 encoding batroxobin-like amino acid sequence is as follows:

```
                                          (SEQ ID NO: 3)
Met-Val-Leu-Ile-Arg-Val-Ile-Ala-Asn-Leu-Gln-Ile-

Leu-Gln-Val-Ser-Thr-Tyr-Ala-Gln-Lys-Ser-Ser-Glu-

Leu-Val-Ile-Gly-Gly-Asp.
```

The assays showed that SL32 had a significantly better ability to hydrolyze the metaglobulin Aαstrand than batroxobin.

The present invention obtained the haemocoagulase by the process of isolating and purifying the venom of Agkistrodon acutus and further obtained its encoding genes. More particularly, the technical solution of the present invention is as follows: isolating and purifying haemocoagulase from snake venom of Agkistrodon acutus, sequencing its N-terminal amino acid sequence, designing and synthesizing the oligonucleotide probes according to the sequence, extracting mRNA from toxic glandular tissues of the Agkistrodon acutus, reversely transcripting mRNA and constructing the cDNA library, screening the cDNA library with the probes above and performing sequencing analysis of the positive clones respectively, and then cloning the target genes which were screened out into the expression vector. (see FIG. 1)

1. Isolation and Purification of Haemocoagulase

Active ingredients with fibrinogen aggregation activity were isolated and concentrated directly from snake venom by using the DEAE Sepharose Fast Flow column, manufactured by GE Healthcare, and isolated by gel filtration chromatography using the Sephacryl S-200HR column, then further collected and purified by using the DEAE 8HR HPLC column manufactured by Waters Corp.

2. Identification of the N-terminal Amino Acid Sequence and Synthesis of the Oligonucleotide Probe The isolated and purified protein mentioned above was performed SDS-PAGE electrophoresis, then transferred to the PVDF memberane. The strip corresponding to the protein was cut and the N-terminal of the peptide chain was determined by Edman degradation using the 120-A gaseous phase sequenator of the American ABI company. According to the sequencing result, the possible nucleotide sequence was deducted and the sequence of the probe is tggtcattggaggtgatgaa (SEQ ID NO: 4). The corresponding oligonucleotide probe was synthesized by using the ABI 3900 gene synthesis machine.

3. Construction of cDNA Library 1 g fresh Agkistrodon acutus glandular tissue was taken and the total RNAs of sample cells were extracted by using the Qiagen RNeasy mini kit, and mRNA was then purified and obtained from the aforementioned total RNAs by using the mRNA Purification Kit. The cDNA was further synthesized by the TimeSaver™ cDNA Synthesis Kit of GE Healthcare. Then both ends of the cDNA were ligated with EcoRI/NotI adapters, and the cDNA with adapters was purified through SizeSep™ 400 Spun Columns of the company. Then the purified cDNA was cloned to a λgt11 vector manufactured by Promega Company by the double enzyme digestion method. After being transformed to E. coli, the experiment was followed by amplification culture, clonal and titre identification.

4. Selection of Positive Clone

The total λDNAs of the cDNA library mentioned above were extracted as a template, the synthesized N-terminal primers (tggtcattggaggtgatgaa (SEQ ID NO: 4)) were labeled with $P^{32}$ by using the HexaLabel™ DNA Labeling Kit made by GE Healthcare. The probe was used for in situ hybridization screen of the cDNA library and the positive bacteria colonies were then selected out.

5. Acquisition of Complete Sequence of Gene Encoding Haemocoagulase Protein

λDNA was extracted from these positive colonies mentioned above after amplification culture, then sequenced with the primers (forward: GGTGGCGACGACTCCTGGAGCCCG (SEQ ID NO: 5), reverse: TTGACACCAGACCAACTGGTAATG (SEQ ID NO: 6)) on plasmid using 3730 Gene sequence analysis of ABI.

6. Construction of Expression Vector, Transformation of the E. coli, Identification of the Positive Clones A primer pair (Forward atggtgctgatcagagtgatagca (SEQ ID NO: 7); Reverse cgggcaagtcgcagttttatt (SEQ ID NO: 8)) was designed to ampilfy ORF of the above-mentioned haemocoagulase.

Amplified product was cloned into the E. coli expression vector pET31b(+) made by Novagen company . Then the expression vecctor was transformed into E. coli host Rosetta (DE3) pLysS, followed with identifying and selecting transformed positive clones by PCR prior to further sequencing identification.

7. Expression of Target Genes and Acquisition of Proteins

The proteins expressed in bacteria were extracted with the BugBuster kit made by Novagen. Studies shows that the mixed solution of 250 mM of NaCl, cyclode-xtrin, GSH/GSSG, EDTA can most effectively promote and produce the SL32 proteins with biological activity among total 96 condition combinations.

Of course, there are some other methods for obtaining the complete sequence of the gene encoding the haemocoagulase, for example, designing and synthesizing upstream and downstream oligonucleotide primers according to the indentified N-terminal amino acid sequence as well as the homology sequences of other snakes. The total mRNA obtained from crotalin glands of Agkistrodon acutus could be used as a template and cDNA could be obtained by reverse transcription, followed by sequencing and designing to synthesize related primers, thereby further cloning the complete gene sequence.

The invention makes use of the unique resources of Agkistrodon acutus in china, to isolate haemocoagulase from the snake venom, and further to obtain the genes of haemocoagulase by cloning, which creates good conditions for the development of genetic engineering products of recombinant haemocoagulase in the future.

DRAWINGS OF INVENTION

MODE OF CARRYING OUT THE INVENTION

Figure 1:
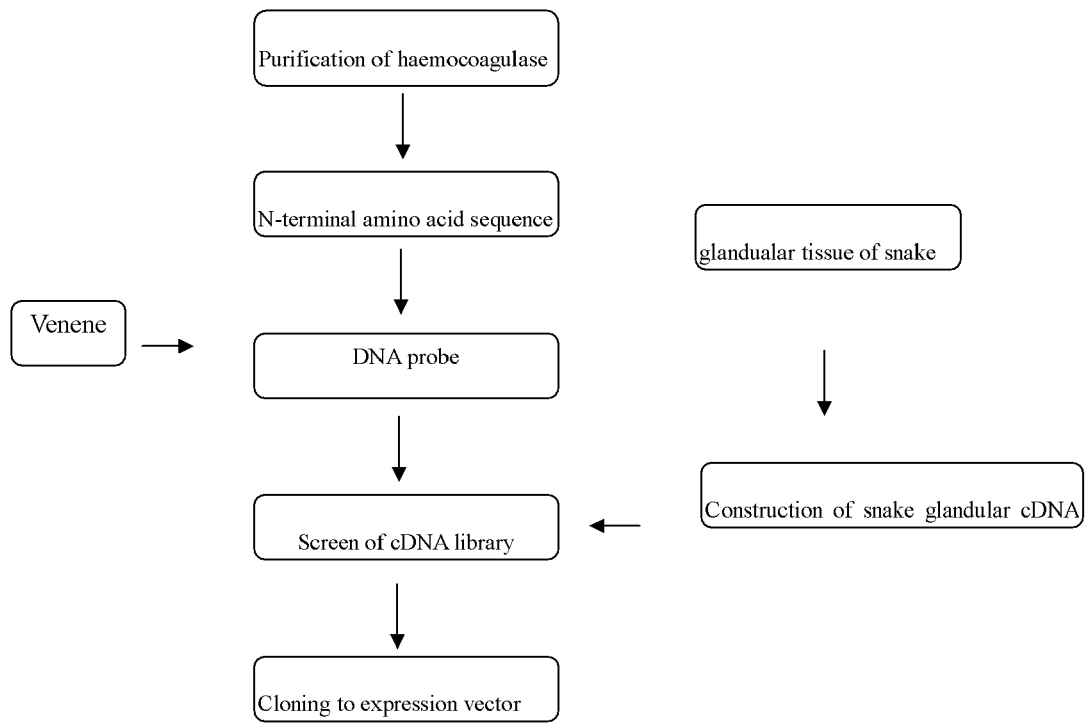
FIG. 1 is a flow diagram of SL32 gene cloning

The present invention will be further illustrated with reference to the examples as follows, but the scope of the present invention is not limited thereto.

EXAMPLE 1

Isolation and Purification of Haemocoagulase

The collected snake venom was dissolved in 0.02 M of Tris-HCl buffer solution with a pH of 8.0 and centrifuged for thirty minutes. The DEAE Sepharose Fast Flow column manufactured by GE Healthcare was balanced with the buffer solution above, to which the supernatent obtained by centrifugation was transferred. The elution was conducted with a linear concentration gradient of NaCl with an eluting temperature of 4° C. and a flow rate of 80 mL/h (starting from a balanced concentration until a concentration of 0.02 M of Tris-HCl, 0.2 M of NaCl and a pH of 8.0). The eluted proteins with respective peak value were collected and the fibrinogen aggregation activity was tested. It has been found that the resulting protein peak eluted at 0.02~0.08 M of NaCl concentration has fibrinogen aggregation activity. The active ingredients were applied to the Sephacryl S-200HR column and isolated by gel filtration chromatography. The elution solution was 0.02 M of the Tris-HCl buffer solution with a pH value of 8.0. The ingredients with fibrinogen aggregation activity (primary eluting peak) were collected and further isolated by the DEAE 8HR HPLC column (The column had been balanced with 0.02 M of Tris-HCl buffer solution with a pH of 8.0 beforehand) manufactured by Waters Corp. The elution solution was the same as the elution solution for DEAE Sepharose Fast Flow column; the protein peak eluted with 0.03-0.06M NaCl solution has fibrinogen aggregation activity; and the purified fractions with fibrinogen aggregation activity (primary eluting peak) were collected.

EXAMPLE 2

Identification of the N-terminal Amino Acid Sequence and Synthesis of the Oligonucleotide Probe The isolated and purified protein above was taken and transferred to the PVDF membrane after SDS-PAGE electrophoresis. The strip corresponding to the protein was cut and the N-terminal of the peptide chain was determined by Edman degradation using 120-A gaseous phase sequenator made by ABI. The N-terminal batroxobin-like 30 amino acid sequence of SL32 was as follows: Met-Val-Leu-Ile-Arg-Val-Ile-Ala-Asn-Leu-Gln-Ile-Leu-Gln-Val-Ser-Thr-Tyr-Ala-Gln-Lys-Ser-Ser-Glu-Leu-Val-Ile-Gly-Gly-Asp (SEQ ID NO: 3). According to the sequencing result, the potential nucleotide sequences were deducted, the hybridization probe was designed on-line by using Primer 3 software, the sequence of the probe was tggtcattggaggtgatgaa (SEQ ID NO: 4), and the corresponding oligonucleotide probe was synthesized by using the ABI 3900 gene synthesis machine.

EXAMPLE 3

Construction of cDNA Library 1 g fresh fresh Agkistrodon acutus tissue was taken; the total RNAs of sample cells were extracted using the Qiagen RNeasy mini kit. The mRNA was purified and obtained from the aforementioned total RNAs by using the mRNA Purification Kit. The cDNA was further synthesized by using of the TimeSaver™ cDNA Synthesis Kit made by GE Healthcare, ligated by EcoRI/NotI adapters at their both ends. The cDNA with adapters were purified by the SizeSep™ 400 Spun Columns of GE Healthcare Company and cloned into the λgt11 vectors manufactured by Promega Company using double enzyme digestion method. The recombinant plasmid was transformed into E coli then followed by amplification culture, clone identification and titer assay.

EXAMPLE 4

Selection of Positive Clone

The total DNA of the cDNA library mentioned above was extracted as a template, the synthesized N-terminal primers mentioned above (tggtcattggaggtgatgaa (SEQ ID NO: 4)) were labeled with $P^{32}$ by using the HexaLabel™ DNA Labeling Kit of GE Healthcare. The probe was used for in situ hybridization screen of the cDNA library and then the positive colonies were selected.

EXAMPLE 5

Acquisition of Complete Sequence of Gene Encoding Haemocoagulase

λDNA was extracted from aforesaid positive colonies after amplification culture, then sequenced with the primer (forward:GGTGGCGACGACTCCTGGAGCCCG (SEQ ID NO: 5), reverse: TTGACA CCAGACCAACTGGTAATG (SEQ ID NO: 6)) on plasmid using the 3730 Gene sequence analysis made by ABI.

EXAMPLE 6

Construction of Expression Vector, Transformation of E. coli, Identification of the Positive Clones A primer Pair (Forward:TCCCCTCTAGAATGGTGCTGATCAGAGTGATAGCAA (SEQ ID NO: 9); Reverse: GGTGCTCGAGTCACGGGCAAGTCGCAGT (SEQ ID NO: 10)) were designed to amplify ORF of the above-metioned haemocoagulase using high fidelity Taq enzyme, the condition of amplification reaction was at 96° C. 2 min, (at 96° C. for 30 s, at 59° C. for 30 s, at 72° C. for 1 min) total 25 cycles, at 72° C. for 7 min, store at 4° C. Xba I and XhoI were used to digest amplified products. Then the digested product was cloned to E. coli expression vector pET31b(+) (Novagen company). The recombinant plasmids were transformed into Ecoli host Rosetta (DE3) pLysS, followed by indentifying and selecting transformed positive clones by PCR prior to further sequencing identification, the sequencing primers are vector self-primers.

```
                                        (SEQ ID NO: 11)
T7 promoter:        TAATACGACTCACTATAG (SEQ ID NO: 12)
T7 terminator:      GCTAGTTATTGCTCAGCGGT
```

EXAMPLE 7

Expression of Target Genes and Acquisition of Proteins

The screened positive clones with encoding mentioned above protein sequences were amplified and cultured respectively. The E coli proteins (inclusion body) were extracted using the BugBuster kit made by Novagen. The iFOLD™ Protein Refolding System 1 for the study of Protein Refolding from Novagen was further used to test the optimum condition for forming the spatial structure of the protein. Studies have found that the mixture solution of 250 mM NaCl, cyclodextrin, GSH/GSSG, EDTA can most effectively stimulate to form SL32 proteins with the biological activity among all 96 condition combinations.

EXAMPLE 8

Analysis and Identification of the SL32 Gene and Its Protein

BLAST result showed that SL32 gene has the highest homology with mRNA of batroxobin (gi:211023). The mRNA sequence of batroxobin has 1504 base pairs, while the SL32 gene whose CDS is (60) . . . (827), has 1326 base pairs altogether. Both SL32 and batroxobin have 255 amino acids. The difference between them lies in that the eleventh N-terminal amino acid is glutamine (Q) in SL32, while it is leucine (L) in the primary structure of batroxobin. Accordingly, the cloned SL32 gene is a wholly novel Haemocoagulase gene.

EXAMPLE 9

Functional Analysis of SL32 Expression Protein

Studies on the pharmacodynamic index, such as the blood coagulation system and the fibrinolytic system have been performed with Japanese albino rabbits and mice. The results showed that:
(1) SL32 has an effect on significant reduction of bleeding time. An intravenous injection of 0.50, 0.25 and 0.125 U/kg of SL32 protein significantly shorten the bleeding time of the mice's cutted tails.
(2) SL32 has an effect on stimulating blood coagulation. An intravenous injection of 0.12, 0.06 and 0.03 U/kg of SL32 protein significantly shorten the whole blood clotting time in the rabbits. The effect is shown 10 minutes after administration; the peak level is reached after half an hour; and the effect lasts for more than 6 hours. The difference between SL32 and positive control drug Reptilase is not significant for the time and the strength of stimulating blood coagulation.
(3) For the allergic test of systemic administration of SL32, SL32 sensitized contact test and provocative contact test on guinea pigs have been observed. No allergy has been found during 28 days observation and the result of allergic test is negative.

(4) For SL32 hemolytic test, no hemolysis and erythrocyte aggregation have been observed from the hemolytic test on rabbit blood in vitro. The result of hemolysis test is negative.

(5) For SL32 vascular stimulation test, administration of the drug by injecting rabbit at ear conch, ear edge vein and quadriceps femoris in order to observe whether SL32 stimulates the above-mentioned tissues or not. The result showed: injection of the product does not cause red swelling, bleeding, denaturation or necrosis of tissues; administration by the routes above is not irritative; and the drug can be administered intravenously or intramuscularly.

(6) For SL32 nervous toxicity, bleeding toxicity and abnormal toxicity tests, the mice, which were intravenously injected SL32, were observed for the nevous toxicity and abnormal toxicity. The mice, which were subcutaneously injected, were observed for bleeding toxicity. The results of the test are negative in the range of observed dosage.

(7) For SL32 acute toxicity test, no adverse reaction has been observed on either rats or mice injected via vena caudalis and muscle once at 50 U/kg (equivalent to 3000 times of the clinical human conventional dose).

(8) For SL32 long term toxicity test, intravenously injected rats with the drug at a dose of 1.36 u, 0.68 u or 0.34 u/kg, no toxic effect has been found in total 22 tissue organs, including the main metabolism and detoxification organs such as kidney, etc., and central nervous system and heart, etc.

Figure 2:
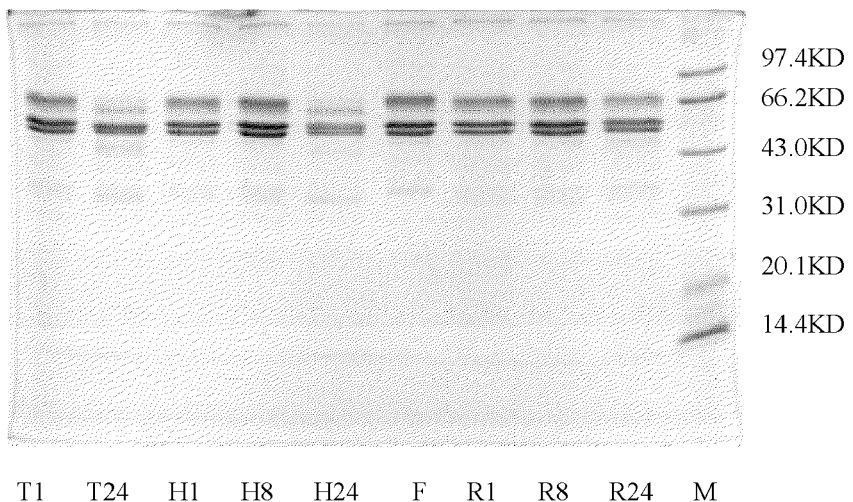
FIG. 2 is a SDS-PAGE analysis electrophoresis picture of hydrolysis of fibrinogen by SL32 and Reptilase, wherein T represents human thrombin, H represents SL32, F represents fibrinogen control, R represents Reptilase, the numbers after these letters represent incubation time (hour), and M represents standard molecular weight.

(9) Under a condition with an equivalent activity, the SDS-PAGE analysis of hydrolyzed fibrinogens with SL32 and Reptilase (see FIG. 2).

The electrophoretic result indicates that SL32 significantly hydrolyze fibrinogen Aα-strand and has a similar strength to human thrombin, while the hydrolysis of fibrinogen Aα-strand with Reptilase is still not evident. That is, SL32 is better than Reptilase in hydrolyzing fibrinogen Aα-strand.

The above results demonstrate that the expression product of SL32 has a significant hemostasis effect. Comparing with Reptilase, it has such features as a broader effective dose range, safer and more reliable application.

INDUSTRIAL APPLICABILITY

The present invention isolates and purifies haemocoagulase from Agkistrodon acutus venene and also finds out and clones its encoding genes. Haemocoagulase of the present invention has an obvious hemostatic effect, a broad effective dose, and safe and reliable application, which creates good conditions for the development of genetic engineering products of recombinant haemocoagulase in the future.

What is claimed:

1. An isolated venene heamocoagulase comprising SEQ ID NO: 2 or a sequence variant thereof, wherein said variant has heamocoagulase activity and is formed by replacement, deletion or addition of one or more amino acids of said SEQ ID NO: 2, with the exception of the amino acid at position 11 which is Gln.

2. A hemostatic pharmaceutical composition comprising the venene haemocoagulase of claim 1.

3. The venene hamocoagulase of claim 1, wherein the sequence variant includes insertion of a Thr between positions 16 and 17 of SEQ ID NO: 2.

4. A venene haemocoagulase isolated from *Agkistrodon acutus* comprising amino acid sequence SEQ ID NO: 2.

5. The venene haemocoagulase of claim 4, further comprising a sequence variant of SEQ ID NO: 2 formed by replacement, deletion, or addition of one or more amino acids of SEQ ID NO: 2, wherein the amino acid at position 11 of the variant of SEQ ID NO: 2 is Gln and wherein said variant possesses haemocoagulase activity.

6. The venene haemocoagulase variant of claim 5, wherein the sequence variant includes insertion of a Thr between positions 16 and 17 of SEQ ID NO: 2.

* * * * *

SEQUENCE LISTING

```
<160> NUMBER OF SEQ ID NOS: 12

<210> SEQ ID NO 1
<211> LENGTH: 1326
<212> TYPE: DNA
<213> ORGANISM: Agkistrodon acutus
<220> FEATURE:
<221> NAME/KEY: CDS
<222> LOCATION: (60)..(827)

<400> SEQUENCE: 1
gttttaagta agggactggg atcttgcagg caaacagctt gccacgcaga gttgaagct        59 atg gtg ctg atc aga gtg ata gca aac ctt cag ata tta cag gtt tct       107
Met Val Leu Ile Arg Val Ile Ala Asn Leu Gln Ile Leu Gln Val Ser
1               5                   10                  15 tac gca caa aag tct tct gaa ctg gtc att gga ggt gat gaa tgt gac       155
Tyr Ala Gln Lys Ser Ser Glu Leu Val Ile Gly Gly Asp Glu Cys Asp
                20                  25                  30 ata aat gaa cat cct ttc ctt gca ttc atg tac tac tct ccc cgg tat       203
Ile Asn Glu His Pro Phe Leu Ala Phe Met Tyr Tyr Ser Pro Arg Tyr
            35                  40                  45 ttc tgt ggt atg act ttg atc aac cag gaa tgg gtg ctg acc gct gca       251
Phe Cys Gly Met Thr Leu Ile Asn Gln Glu Trp Val Leu Thr Ala Ala
        50                  55                  60 cac tgt aac agg aga ttt atg cgc ata cac ctt ggt aaa cat gcc gga       299
His Cys Asn Arg Arg Phe Met Arg Ile His Leu Gly Lys His Ala Gly
65                  70                  75                  80 agt gta gca aat tat gat gag gtg gta aga tac cca aag gag aag ttc       347
Ser Val Ala Asn Tyr Asp Glu Val Val Arg Tyr Pro Lys Glu Lys Phe
                85                  90                  95 att tgt ccc aat aag aaa aaa aat gtc ata acg gac aag gac att atg       395
Ile Cys Pro Asn Lys Lys Lys Asn Val Ile Thr Asp Lys Asp Ile Met
                100                 105                 110 ttg atc agg ctg gac aga cct gtc aaa aac agt gaa cac atc gcg cct       443
```

```
                Leu Ile Arg Leu Asp Arg Pro Val Lys Asn Ser Glu His Ile Ala Pro
                    115                 120                 125 ctc agc ttg cct tcc aac cct ccc agt gtg ggc tca gtt tgc cgt att           491
Leu Ser Leu Pro Ser Asn Pro Pro Ser Val Gly Ser Val Cys Arg Ile
130                 135                 140 atg gga tgg ggc gca atc aca act tct gaa gac act tat ccc gat gtc           539
Met Gly Trp Gly Ala Ile Thr Thr Ser Glu Asp Thr Tyr Pro Asp Val
145                 150                 155                 160 cct cat tgt gct aac att aac ctg ttc aat aat acg gtg tgt cgt gaa           587
Pro His Cys Ala Asn Ile Asn Leu Phe Asn Asn Thr Val Cys Arg Glu
                165                 170                 175 gct tac aat ggg ttg ccg gcg aaa aca ttg tgt gca ggt gtc ctg caa           635
Ala Tyr Asn Gly Leu Pro Ala Lys Thr Leu Cys Ala Gly Val Leu Gln
                180                 185                 190 gga ggc ata gat aca tgt ggg ggt gac tct ggg gga ccc ctc atc tgt           683
Gly Gly Ile Asp Thr Cys Gly Gly Asp Ser Gly Gly Pro Leu Ile Cys
                195                 200                 205 aat gga caa ttc cag ggc att tta tct tgg gga agt gat ccc tgt gcc           731
Asn Gly Gln Phe Gln Gly Ile Leu Ser Trp Gly Ser Asp Pro Cys Ala
210                 215                 220 gaa ccg cgt aag cct gcc ttc tac acc aag gtc ttt gat tat ctt ccc           779
Glu Pro Arg Lys Pro Ala Phe Tyr Thr Lys Val Phe Asp Tyr Leu Pro
225                 230                 235                 240 tgg atc cag agc att att gca gga aat aaa act gcg act tgc ccg tga           827
Trp Ile Gln Ser Ile Ile Ala Gly Asn Lys Thr Ala Thr Cys Pro
                245                 250                 255 aaacctttga aaaggttaag aggcgaaagt gttaacatat tagttcatct cttctatatc         887
cctaaccata tccaactaca ttggaatata ttcccagatc gtaagctttt tttagactca         947
aataggactg cctttggaat aagaaatgct caaaacagtg gtgcagggat gatgaggcct        1007
gttttatggt gaggtgcaaa atttctgac tctaaaaagg accattccaa atattttaac        1067
catttctgtc cacttctggg acagtgtggt ccttgatgct ctctgagctt gtcttcttgc        1127
agacgtttca ctacccagct aggtaatatc atcagtgcta gaatattctc ttctatgtta        1187
gttttgtggc atttacaata cgctcatatg tagccatgca gtcaccccac aaacatatcc        1247
atgtacccgg gtcccaccgt tgcataaaaa ggatcccaga ttaactccac ttcccaatca        1307
cgaaatagaa tcttttgag                                                    1326

<210> SEQ ID NO 2
<211> LENGTH: 255
<212> TYPE: PRT
<213> ORGANISM: Agkistrodon acutus

<400> SEQUENCE: 2

Met Val Leu Ile Arg Val Ile Ala Asn Leu Gln Ile Leu Gln Val Ser
1               5                   10                  15

Tyr Ala Gln Lys Ser Ser Glu Leu Val Ile Gly Gly Asp Glu Cys Asp
                20                  25                  30

Ile Asn Glu His Pro Phe Leu Ala Phe Met Tyr Tyr Ser Pro Arg Tyr
            35                  40                  45

Phe Cys Gly Met Thr Leu Ile Asn Gln Glu Trp Val Leu Thr Ala Ala
    50                  55                  60

His Cys Asn Arg Arg Phe Met Arg Ile His Leu Gly Lys His Ala Gly
65                  70                  75                  80

Ser Val Ala Asn Tyr Asp Glu Val Val Arg Tyr Pro Lys Glu Lys Phe
                85                  90                  95

Ile Cys Pro Asn Lys Lys Lys Asn Val Ile Thr Asp Lys Asp Ile Met
```

```
                    100                 105                 110
Leu Ile Arg Leu Asp Arg Pro Val Lys Asn Ser Glu His Ile Ala Pro
            115                 120                 125

Leu Ser Leu Pro Ser Asn Pro Pro Ser Val Gly Ser Val Cys Arg Ile
        130                 135                 140

Met Gly Trp Gly Ala Ile Thr Thr Ser Glu Asp Thr Tyr Pro Asp Val
145                 150                 155                 160

Pro His Cys Ala Asn Ile Asn Leu Phe Asn Asn Thr Val Cys Arg Glu
                165                 170                 175

Ala Tyr Asn Gly Leu Pro Ala Lys Thr Leu Cys Ala Gly Val Leu Gln
            180                 185                 190

Gly Gly Ile Asp Thr Cys Gly Gly Asp Ser Gly Gly Pro Leu Ile Cys
        195                 200                 205

Asn Gly Gln Phe Gln Gly Ile Leu Ser Trp Gly Ser Asp Pro Cys Ala
    210                 215                 220

Glu Pro Arg Lys Pro Ala Phe Tyr Thr Lys Val Phe Asp Tyr Leu Pro
225                 230                 235                 240

Trp Ile Gln Ser Ile Ile Ala Gly Asn Lys Thr Ala Thr Cys Pro
                245                 250                 255

<210> SEQ ID NO 3
<211> LENGTH: 30
<212> TYPE: PRT
<213> ORGANISM: Agkistrodon acutus

<400> SEQUENCE: 3

Met Val Leu Ile Arg Val Ile Ala Asn Leu Gln Ile Leu Gln Val Ser
1               5                   10                  15

Thr Tyr Ala Gln Lys Ser Ser Glu Leu Val Ile Gly Gly Asp
            20                  25                  30

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
tggtcattgg aggtgatgaa                                             20

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggtggcgacg actcctggag cccg                                        24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
```

```
ttgacaccag accaactggt aatg                                              24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atggtgctga tcagagtgat agca                                              24

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgggcaagtc gcagttttat t                                                 21

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcccctctag aatggtgctg atcagagtga tagcaa                                 36

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggtgctcgag tcacgggcaa gtcgcagt                                          28

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
taatacgact cactatag                                                     18

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gctagttatt gctcagcggt                                                   20
```